United States Patent [19]

Crovetti et al.

[11] 4,061,764

[45] Dec. 6, 1977

[54] CERTAIN O-SUBSTITUTED THIOPHENE OXIME CARBAMATES USED AS ANTIBACTERIAL AND ANTIFUNGAL AGENTS

[75] Inventors: Aldo Joseph Crovetti, Lake Forest, Ill.; Robert George Stein, Kenosha, Wis.

[73] Assignee: Abbott Laboratories, North Chicago, Ill.

[21] Appl. No.: 578,792

[22] Filed: May 19, 1975

Related U.S. Application Data

[63] Continuation-in-part of Ser. No. 385,020, Aug. 2, 1972, abandoned, which is a continuation-in-part of Ser. No. 201,184, Nov. 22, 1971, abandoned.

[51] Int. Cl.$^2$ ............................................. A01N 9/12
[52] U.S. Cl. ..................................................... 424/275
[58] Field of Search ........................................ 424/275

[56] References Cited

U.S. PATENT DOCUMENTS

| 3,223,733 | 12/1965 | Heiss et al. ................ 424/275 X |
| 3,639,611 | 2/1972 | Kay ............................... 424/275 |

Primary Examiner—Leonard Schenkman
Attorney, Agent, or Firm—Robert L. Niblack; Vincent A. Mallare

[57] ABSTRACT

Covers use of O-substituted thiophene oxime carbamates as antibacterial and antifungal agents.

7 Claims, No Drawings

CERTAIN O-SUBSTITUTED THIOPHENE OXIME CARBAMATES USED AS ANTIBACTERIAL AND ANTIFUNGAL AGENTS

REFERENCE TO RELATED APPLICATIONS

This application is a continuation-in-part of U.S. Ser. No. 385,020, filed Aug. 2, 1972 now abandoned which is a continuation-in-part of U.S. Ser. No. 201,184 filed Nov. 22, 1971, now abandoned.

SUMMRY OF THE INVENTION

This invention pertains to compounds useful in controlling microorganisms and is more particularly directed to the use as antibacterial and antifungal agents of O-substituted thiophene oxime carbamates of the formula:

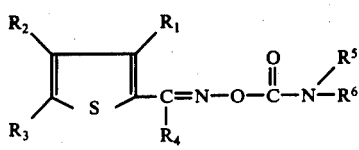

wherein $R^1$, $R^2$ and $R^3$ are selected from the group consisting of hydrogen, loweralkyl, halo, nitro and cyano, $R^4$ is selected from the group consisting of hydrogen, loweralkyl, aryl, alkylthio, arylthio, substituted arylthio, cyano and halogenated loweralkyl, and $R^5$ and $R^6$ are selected from the group consisting of hydrogen, alkyl, aryl, substituted aryl, napthyl and loweralkenyl; with the proviso that when $R^3$ is loweralkyl and none of $R^1$ and $R^2$ are nitro, at least one of $R^5$ and $R^6$ should be selected from the group consisting of aryl, substituted aryl, napthyl, and alkenyl.

DETAILED DESCRIPTION OF THE INVENTION

The O-substituted thiophene oxime carbamates represented by the above general structural formula may be prepared by a variety of methods. However, they are most conveniently prepared by reacting a thiophene ketone or aldehyde with an appropriate reagent to produce the corresponding oxime by well-known procedures. The oxime derivative in turn is approximately reacted in order to produce the thiophene oxime carbamates.

Preferred final compounds of the invention generally fall into four groups. Group 1 includes those compounds where $R^1$, $R^2$ or $R^3$ are nitro, $R^4$ is hydrogen, or loweralkyl, $R^5$ is hydrogen and $R^6$ is aryl, substituted aryl, naphthyl or loweralkyl. Another preferred group of compounds are those where $R^1$, $R^2$ or $R^3$ is halo, $R^4$ is hydrogen, loweralkyl, alkylthio or arylthio, $R^5$ is hydrogen, and $R^6$ is loweralkyl, aryl or substituted aryl. Yet another preferred group of compounds are those where $R^1$, $R^2$ or $R^3$ is loweralkyl, $R^4$ is loweralkyl, $R^5$ is hydrogen and $R^6$ is loweralkyl or substituted aryl. The last preferred group of compounds include those where $R^1$, $R^2$ and $R^3$ are hydrogen, $R^4$ is hydrogen, loweralkyl, or cyano, $R^5$ is hydrogen and $R^6$ is loweralkyl or aryl.

Representative oximes and intermediates thereof falling within the just set-out formula were prepared as outlined in the examples below.

EXAMPLE 1

2-Thienylhydroxamic Chloride

To a stirred solution of 12.7 g. (0.10 mole) of at 95°–97° C.
Analysis: Calcd: Cl, 21.9;
Found: Cl, 21.8%.

EXAMPLE 2

5-Nitro-2-Thienylhydroxamic Chloride

To a stirred solution of 12.7 g. (0.10 mole) of 2-thiophencarboxaldoxamine in 300 ml. of dry ether was added 6.86 g.(0.11 mole) of nitrosyl chloride in 100 ml. of dry ether over a period of 10 minutes at 0° C. One hour after this addition the temperature was allowed to rise to 20° C. over 1 hour period. The ether was then removed in vacuo and the resulting yellow-orange residue was crystallized from methylene chloride to give 8.9 g. of product melting at 95°–97° C.
Analysis: Calcd: Cl, 21.9; Found: Cl, 21.8%.

EXAMPLE 2

5-Nitro-2-Thienylhydroxamic Chloride

Here the procedure of Example 1 was utilized to prepare the above hydroxamic chloride from 5-nitro-2-thiophenecarboxaldoxamine. The product melted at 147°–149° C. after being recrystalized from methylene chloride.
Analysis: Calcd: C, 29.06; H, 1.46; N, 13.56; Cl, 17.15; Found: C, 29.17; H, 1.44; N, 13.45; Cl, 17.03.

Alpha-Oximino-2-Thienylacetonitrile

To a stirred solution of 2.3 g. (0.10 mole) of sodium metal dissolved in 50 ml. ethanol and cooled to 0° C. in an ice bath was added 12.3 g. (0.10 mole) of 2-thienylacetonitrile. After the addition was complete 10.3 g. (0.10 mole) of butylnitrite was added. The reaction was stirred 1 hour at 0° C. and 3 hours at room temperature before the mixture was concentrated to dryness in vacuo. The residue was washed with ether. The sodium salt of the product was dissolved in water and acidified with concentrated hydrochloric acid to a pH of 3. The solid was filtered, washed with water, dried and recrystallized from chloroform to give 6.6 g. of final product which melted at 135°–137° C.
Analysis: Calcd: C, 47.37; H, 2.65; N, 18.42; Found: C, 47.51; H, 2.63; N, 18.60.

EXAMPLE 4

5-Acetyl, 2-Chloro-3-Nitro Thiopheneketoxime

A mixture of 26 g. (0.126 mole) of 5-acetyl, 2-chloro-3-nitro thiophene and 10.5 g. (0.15 mole) of hydroxylamine hydrochloride was refluxed 5 hours in 200 ml. of ethanol. The solution was concentrated under vacuo, the residue washed with water and then dried. After recrystallization from ethyl acetate 14 g. of the ketoxime was obtained which melted at 172°–176° C.
Analysis: Calcd: C, 32.67; H, 2.28; N, 12.69; Found: C, 32.52; H, 2.16; N, 12.60.

EXAMPLE 5

5-Chloro-2-(Alpha, Alpha, Alpha-Trifluoroacetyl) Thiopheneketoxime

A mixture of 25 g. (0.11 mole) of 5-chloro-2-(alpha, alpha, alpha-trifluoroacetyl) thiophene, and 10 g. (0.14 mole) of hydroxylamine hydrochloride was refluxed for 12 hours in a 50-50 solution of ethanol and water. The solution was cooled and 5.6 g. (0.14 mole) of sodium hydroxide dissolved in 50 ml. water was then added. The solution was concentrated to dryness and the residue was washed with water, dried and recrystallized from benzene to give 18.5 g. of product, which melted at 123°-125° C.

Analysis: Calcd: C, 31.38; H, 1.31; N, 6.09; Found: C, 13.67; H, 1.37; N, 6.14.

EXAMPLE 6

Gamma-Methyl,5-Chloro-Thienylthiohydroximate

To a solution of 19.5 g. (0.10 mole) of 5-chloro-2-thienylhydroxamic chloride and 9.6 g. methyl mercaptan (0.20 mole) in 150 ml. of dry ether cooled to 0° C. was added 15.6 (0.15 mole) of triethylamine over a period of 10 minutes. The reaction mixture was stirred for 1 hour at room temperature. The mixture was then poured into 250 ml. of 0.5N sulfuric acid. The aqueous base was extracted several times with ether and the ether wash was combined and thereafter washed several times with water. The ehter solution was dried, and the filtrate concentrated to give a low melting solid. One recrystallization from cyclohexane gave 11.5 g. of product which melted at 53°-55° C.

Analysis: Calcd: C, 34.69; H, 2.90; N, 6.74; Found: C, 34.50; H, 2.81; N, 6.76.

EXAMPLE 7

Gamma-Phenyl-5-Chloro-2-Thienylthiohydroximate

To a solution of 5.58 g. (0.03 mole) of 5-chloro-2-thienylhydroxamic chloride in 33 g. (0.03 mole) of thiophenol in 100 ml. of ether at 0° C. was added 5.01 g. (0.05 mole) of triethylamine. The mixture was stirred 1 hour and then poured into 50 ml. of 0.5N sulfuric acid. The aqueous phase was then washed several times with ether. The ether washings were combined, washed with water, dried and concentrated to a solid. Recrystallization from cyclohexane gave 5.4 g. of a solid melting at 95°-97° C.

Analysis: Calcd: C, 48.97; H, 2.98; N, 5.19; Found: C, 49.08; H, 3.04; N, 5.29.

Additional oximes were prepared according to the procedures set out in Examples 1-7. These compounds are characterized in Table I below.

TABLE I

| Example No. | $R_3$ | $R^2$ | $R^1$ | $R^4$ | M.P. |
|---|---|---|---|---|---|
| 8 | H | H | H | H | 128 |
| 9 | H | H | H | $CH_3$ | 112-113 |
| 10 | H | H | H | $C_2H_5$ | 55-56 |
| 11 | H | H | H | $C_3H_7$ | 57 |
| 12 | Br | H | H | H | 138-139 |
| 13 | $NO_2$ | H | H | H | 157-158 |
| 14 | $NO_2$ | H | H | $CH_3$ | 189 |
| 15 | $CH_3$ | H | H | H | 79-81 |
| 16 | $CH_3$ | H | H | $CH_3$ | 125 |
| 17 | Cl | H | H | H | 122-125 |
| 18 | Cl | H | H | $CH_3$ | 159-160 |
| 19 | Cl | H | H | Cl | 121-122.5 |

The above oximes or others are then reacted with an isocyanate to produce the desired final products. The entire general reaction scheme then is as follows:

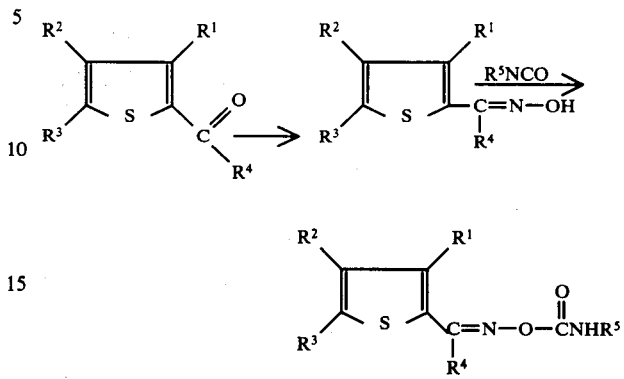

The general procedure then in preparing the compounds of the invention may be set out as follows: To a solution of one part of a thiopheneoxime dissolved in a suitable aprotic solvent containing a catalytic amount of a tertiary amine is added one part of an isocyanate. The resulting solution is stirred for a few hours and the product removed by filtration, if insoluble in the reaction solution. If the product is soluble in the reaction media the solvent is removed in vacuo and the desired product is crystallized from an appropriate solvent. Typical aprotic reaction solvents include ether, benzene, chloroform, carbon tetrachloride, methylene dichloride, acetone, etc. Representative tertiary amines useful as catalysts include pyridine, triethylamine, etc.

The following examples illustrate typical products of the invention and their method of preparation.

EXAMPLE 20

O(Methyl Carbamoyl) 5-Nitro-2-Thiophenecarboxaldoxime

To a solution of 12 g. (0.07 mole) of 5-nitro-2-thiophenecarboxaldoxime in 50 ml. of ether was added 4 g. (0.07 mole) of methylisocyanate in 25 ml. of ether. A precipitate formed immediately and stirring was continued for 1 hour after the addition was complete. The product was filtered, washed with ether, and recrystallized from benzene to give 13.5 g. of product melting at 104-105 dec.

EXAMPLE 21

O(3-Chlorophenyl Carbamoyl)-2-Acetylthiophene Ketoxime

To a solution of 7.05 (0.05 mole) of 2-acetylthiophene ketoxime and 2 drops of triethylamine in 100 ml. of benzene was added 7.65 g. (0.05 mole) of 3-chlorophenylisocyanate. The solution was stirred for 2 hours and concentrated in vacuo to give a solid. One crystallization from benzene gave 11 g. of product melting at 138°-140° C.

EXAMPLE 22

O-(Methylcarbamoyl)2-Acetyl5-Chloro-4-Nitro-Thiopheneketoxime

To a solution of 4.4 g. (0.02 mole) of 2-acetyl-5-chloro-4-nitro-thiopheneketoxime in 50 ml. of ether was added 1.14 (0.02 mole) of methylisocyanate in 10 ml. of ether. The solution was stirred 2 hours and then concentrated in vacuo to dryness. The product was crystallized from ethyl acetate to give 3.1 g. of product melting at 163°–165° C.

EXAMPLE 23

O-(Methylcarbamoyl) Alpha-Oximino-2-Thienylacetonitrile

To a solution of 3.04 g. (0.02 mole) of alphaoximino-2-thienylacetonitrile and 2 drops of triethylamine in 50 ml. of ether was added 1.14 g. (0.02 mole) of methylisocyanate in 10 ml. of ether. After 1 hour the solid was filtered and crystallized from benzene to give 3.8 g. of product melting at 154°–155° C.

Additional compounds of the invention were made according to the techniques of examples 20–23 and these products as well as the products of examples of 20–23 are characterized in Table II below.

TABLE II

| Ex. No. | $R^3$ | $R^2$ | $R^1$ | $R^4$ | $R^5$ | $R^6$ | (C) Analysis Theory/Found | (H) | (N) | M.p. | Yield | Formula |
|---|---|---|---|---|---|---|---|---|---|---|---|---|
| 24 | H | H | H | H | H | $CH_3$ | 45.67 / 45.62 | 4.38 / 4.39 | 15.21 / 15.31 | 122–133 | 88% | $C_7H_8N_2O_2S$ |
| 20 | $NO_2$ | H | H | H | H | $CH_3$ | 36.69 / 36.75 | 3.08 / 3.01 | 18.34 / 18.4 | 104–105 | 81 | $C_7H_7N_3O_4S$ |
| 25 | Br | H | H | H | H | $CH_3$ | 31.95 / 31.81 | 2.67 / 2.64 | 10.64 / 10.67 | 130–131 | 80 | $C_7H_7BrN_2O_2S$ |
| 26 | Cl | H | H | H | H | $CH_3$ | 38.45 / 38.58 | 3.22 / 3.27 | 12.80 / 12.94 | 129–130 | 78 | $C_7H_7ClN_2O_2S$ |
| 27 | $NO_2$ | H | H | H | H |  | 49.47 / 49.17 | 3.12 / 3.01 | 14.43 / 14.47 | 111–112 | 75 | $C_{12}H_9N_{3/04}S$ |
| 28 | $NO_2$ | H | H | $CH_3$ | H | $CH_3$ | 39.31 / 39.25 | 3.73 / 3.73 | 17.28 / 17.30 | 155–166 | 18 | $C_8H_9N_3O_4S$ |
| 29 | $NO_2$ | H | H | H | H | 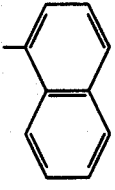 | 56.31 / 56.01 | 3.25 / 3.21 | 12.31 / 12.30 | 140–143 | 36 | $C_{16}H_{11}N_3O_4S$ |
| 30 | $NO_2$ | H | H | H | H | 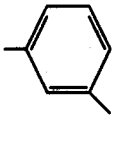 | 44.24 / 44.45 | 2.47 / 2.49 | 12.90 / 12.71 | 166–119 | 31 | $C_{12}H_8ClN_3O_4S$ |
| 31 | Cl | H | H | H | H |  | 51.34 / 51.28 | 3.23 / 3.21 | 9.97 / 9.98 | 99–100 | 50 | $C_{12}H_9ClN_2O_2S$ |
| 21 | H | H | H | $CH_3$ | H | 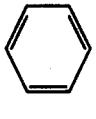 | 59.99 / 60.29 | 4.65 / 4.72 | 10.77 / 10.75 | 167–168.5 | 66 | $C_{13}H_{12}N_2O_2S$ |
| 32 | $NO_2$ | H | H | H | H | 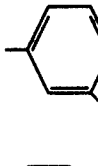 | 40.02 / 39.90 | 1.92 / 1.93 | 11.66 / 11.82 | 158–161 | 60 | $C_{12}H_7Cl_2N_3O_4S$ |
| 33 | H | H | H | H | H | 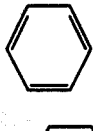 | 58.53 / 58.77 | 4.09 / 4.07 | 11.38 / 11.54 | 100 | 65 | $C_{12}H_{10}N_2O_2S$ |
| 34 | H | H | H | $CH_3$ | H | 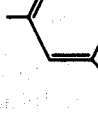 | 47.43 / 47.43 | 3.06 / 3.03 | 8.50 / 8.53 | 143–144 | 38 | $C_{13}H_{10}Cl_2N_2O_2S$ |

TABLE II-continued

| Ex. No. | R³ | R² | R¹ | R⁴ | R⁵ | R⁶ | Analysis Theory/Found (C) | (H) | (N) | M.p. | Yield | Formula |
|---|---|---|---|---|---|---|---|---|---|---|---|---|
| 35 | H | H | H | CH₃ | H | 3-Cl-C₆H₄ | 52.97 / 53.46 | 3.75 / 3.80 | 9.50 / 9.51 | 138-140 | 75 | C₁₃H₁₁ClN₂O₂S |
| 36 | H | H | H | CH₃ | H | CH₂CH=CH₂ | 53.57 / 53.84 | 5.39 / 5.44 | 12.50 / 12.70 | 67-69 | 44 | C₁₀H₁₂N₂O₂S |
| 37 | H | H | H | CH₃ | H | naphthyl | 65.80 / 65.70 | 4.55 / 4.51 | 9.03 / 8.98 | 158-160 | 40 | C₁₇H₁₄N₂O₂S |
| 38 | H | H | H | C₂H₅ | H | 3-Cl-C₆H₄ | 54.45 / 53.90 | 4.24 / 4.22 | 9.06 / 9.06 | 128.5-130 | 26 | C₁₄H₁₃ClN₂O₂S |
| 39 | Cl | H | H | CH₃ | H | 3,4-di-Cl-C₆H₃ | 42.94 / 43.42 | 2.49 / 2.55 | 7.70 / 7.79 | 127-149 | 51 | C₁₃H₉Cl₃N₂O₂S |
| 40 | CH₃ | H | H | CH₃ | H | 2,3-di-Cl-C₆H₃ | 48.99 / 49.32 | 3.52 / 3.60 | 8.15 / 8.28 | 145-147 | 61 | C₁₄H₁₂Cl₂N₂O₂S |
| 41 | CH₃ | H | H | H | H | CH₃ | 48.47 / 48.74 | 5.08 / 5.28 | 14.12 / 14.22 | 105-107 | 58 | C₈H₁₀N₂O₂S |
| 42 | CH₃ | H | H | H | H | 2,3-di-Cl-C₆H₃ | 47.43 / 47.51 | 3.06 / 3.12 | 8.50 / 8.53 | 143-145 | 38 | C₁₃H₁₀Cl₂N₂O₂S |
| 43 | Cl | H | H | CH₃ | H | cyclohexyl | 52.97 / 53.83 | 3.75 / 3.80 | 9.50 / 9.59 | 125-129 | 52 | C₁₃H₁₁ClN₂O₂S |
| 22 | Cl | NO₂ | H | CH₃ | H | CH₃ | 34.60 / 34.75 | 2.90 / 2.91 | 15.12 / 15.29 | 163-165 | 60 | C₈H₈ClN₃O₄S |
| 28 | Cl | H | H | CF₃ | H | CH₃ | 33.52 / 33.73 | 2.10 / 2.12 | 9.76 / 9.73 | 101-103 | 92 | C₈H₆ClF₃N₂O₂S |
| 23 | H | H | H | CN | H | CH₃ | 45.94 / 46.26 | 3.37 / 3.40 | 20.09 / 20.19 | 154-155 | 90 | C₈H₇N₃O₂S |
| 44 | Cl | H | H | CH₃S— | H | CH₃ | 36.29 / 35.92 | 3.42 / 3.46 | 10.57 / 10.59 | 133-134 | 55 | C₈H₉ClN₂O₂S |
| 45 | Cl | H | H | C₆H₅-S- | H | CH₃ | 47.77 / 47.45 | 3.39 / 3.36 | 8.56 / 8.56 | 83-85 | 86 | C₁₃H₁₁ClN₂O₂S₂ |

Representative compounds of the group found useful here were first tested for antibacterial activity. In this test, the medium was a B.B.L. Mueller-Hinton Medium with 0.5% extra agar. The medium was autoclaved for 8 minutes under 15 lbs. of pressure.

A number of organisms were used in preparing the inoculum. These organisms were as follows:

1. *Staphylococcus aureus*
2. *Pseudomonas aeruginosa*
3. *Proteus vulgaris*
4. *Proteus mirabilis*
5. *Escherichia coli*
6. *Salmonella typhimurium*

In each case, a 24 hour culture is grown in a broth comprising 0.3% tryptone, 0.3% beef extract, 0.1% glycose and 0.1% yeast extract in tap water. The culture grown at 37° C. is prepared for the test by making a 1:100 dilution in distilled water.

The drug is prepared as follows: In case of a dry sample, 50 mlg. of the compound is weighed into a sterile screw-capped tube. 0.25 ml. of dimethylformamide is used as the solvent. 0.75 ml. of water is added to each tube to give a 5,000 meg/ml. stock. In case of a liquid sample of drug, it is treated the same as a dry sample except that 0.05 ml. of the compound is used.

The test procedure is as follows. The following amounts of each sample are added to sterile petri dishes:

2.0 ml. of 5000 meg/ml. stock to give 1000 ppm.
2.0 ml. of 500 meg/ml. stock to give 100 ppm.
0.2 ml. of 500 meg/ml. stock to give 10 ppm.

10 ml. of the Mueller-Hinton agar is added to each plate and the plates rotated to mix thoroughly. Two control plates (no drug) are used for each test, one at the beginning and the other at the end. A loopful of each diluted culture is placed on the agar surface and the plates are incubated at 32° C. for 24 hours and then read for presence or absence of bacterial growth. Activities are read as follows. When the compound is active at 1000 ppm. it is given a rating of 1. When the compound is active at 100 ppm. it is given a rating of 2, and when the compound is active at 10 ppm. it is given a rating of 5. No activity is a 0 rating.

The following test results are given with respect to various compounds of the invention. The number given in the second heading relates to the particular organism used in the order given above. Thus, for example, the first organism in which the drug is tested is *Staphylococcus Aureus,* and so forth. Table III below gives the results of the antibacterial tests. The organism number corresponds to the same organism as numbered above.

TABLE III

| Example | Organism | | | | | |
|---|---|---|---|---|---|---|
| | 1 | 2 | 3 | 4 | 5 | 6 |
| 20 | 5 | 2 | 5 | 2 | 2 | 5 |
| 25 | 1 | 0 | 1 | 0 | 1 | 1 |
| 26 | 5 | 2 | 2 | 2 | 2 | 2 |
| 27 | 5 | 1 | 1 | 1 | 1 | 1 |
| 28 | 2 | 1 | 2 | 2 | 2 | 2 |
| 29 | 2 | 2 | 2 | 2 | 2 | 2 |
| 31 | 5 | 2 | 2 | 2 | 2 | 2 |
| 32 | 2 | 0 | 1 | 1 | 1 | 1 |
| 27 | 2 | 0 | 1 | 1 | 1 | 1 |
| 22 | 1 | 1 | 1 | 1 | 1 | 1 |

In another series of tests, many compounds here were also tested for their antifungal activity. In this test procedure, the medium was Difco Saboraud's Liquid Medium with 1.5% agar added. The medium was autoclaved for 15 minutes at 15 lbs. of pressure.

The following molds were used in the tests:
1. *Chaetomium globosum*
2. *Myrothecium verrucaria*
3. *Aspergillus versicolor*
4. *Penicillium citrinum*
5. *Fusarium oxysporum*
6. *Alternaria*
7. *Rhizopus nigricans*

The molds were grown as follows. A seven day mold slant grown at 28° C. on starvation medium (4% dextrose, 1% yeast extract and 1.5 g. of agar per 1 liter of water) is scraped and suspended in approximately 2 ml. Saboraud's broth. The spore suspension is adjusted to equal the No. 1 MacFarland Standard Nephalometer tube using Saboraud's broth as the diluent.

The drugs were prepared and added to sterile petri dishes in exactly the same fashion as in the test for antibacterial activity set out above.

10 ml. of Saboraud's agar is added to each plate and the plates rotated to mix thoroughly. Two control (no drug) plates are used for each test, one at the beginning and the other at the end. Cotton swabs are used to streak the inoculum (6 molds) on the plates. After 3 days incubation at 28° C., the plates are read for growth or absence of growth of the 6 molds. *Rhizopus Nigricans* suspension is inoculated (1 drop) only to the plates that show activity after 3 days incubation. The plates are then re-incubated for 4 days.

Again, a rating of 0 indicates no activity, a rating of 1 indicates activity at 1000 ppm; a rating of 2 indicates activity at 100 ppm and a rating of 5 indicates activity at 10 ppm.

Table IV shows results of the antifungal activity of various compounds. Again, the organism number refers to the organism as listed above.

TABLE IV

| Example | Organism | | | | | | |
|---|---|---|---|---|---|---|---|
| | 1 | 2 | 3 | 4 | 5 | 6 | 7 |
| 23 | 1 | 1 | 1 | 1 | 1 | 1 | 0 |
| 20 | 5 | 5 | 2 | 2 | 5 | 5 | 2 |
| 24 | 1 | 1 | 1 | 1 | 1 | 1 | 1 |
| 25 | 1 | 1 | 1 | 1 | 1 | 1 | 1 |
| 26 | 5 | 2 | 2 | 2 | 2 | 5 | 2 |
| 27 | 2 | 2 | 1 | 1 | 1 | 2 | 1 |
| 28 | 5 | 2 | 2 | 2 | 2 | 5 | 1 |
| 29 | 5 | 2 | 2 | 2 | 2 | 2 | 1 |
| 31 | 2 | 5 | 2 | 2 | 2 | 5 | 2 |
| 32 | 1 | 0 | 0 | 0 | 0 | 1 | 1 |
| 37 | 1 | 1 | 0 | 0 | 0 | 1 | 1 |
| 44 | 1 | 1 | 1 | 1 | 1 | 1 | 1 |
| 28 | 2 | 2 | 1 | 1 | 1 | 1 | 1 |
| 22 | 2 | 1 | 1 | 1 | 1 | 2 | 1 |

In order to inhibit the growth of microorganisms such as fungi and bacteria, one need only apply thereto a small but effective amount of a compound falling within the above formula. The invention is particularly useful in destroying microorganisms found in agriculture. They may also be used to sterilize articles, large areas such as hospital rooms, in detergents and cosmetic preparations, and for any use which requires suitable control of bacteria and/or fungi. When the compounds here are used in agriculture they may be applied to the soil or plants.

When the compounds of this invention are applied as such to the soil, they are ordinarily and preferably combined with an inert adjuvant carrier and applied as a solution, emulsion, suspension, or dust. Aqueous emulsions or suspensions that contain about 0.001 percent to 1 percent by weight, and preferably 0.01 percent to 0.5 percent by weight, of the active agent are particularly suitable for this use. These compositions may also contain about 0.01 percent to 0.1 percent by weight of a wetting agent, such as an alkyl sulfate, an alkyl aryl sulfonate, a sulfosuccinate, a polyethylene glycol ether, and the like. Alternatively, the compounds may be dissolved in an organic solvent, such as acetone, naphtha, ethylene chloride, or kerosene, and applied as solutions, or they may be mixed with or deposited upon such finely-divided solid carriers as clay, chalk, bentonite, talc, kaolin, fullers' earth, and the like and applied as dusts.

The compounds may also be applied by known techniques to plants, to plant seeds, or to the soil in which plants are growing or are to be grown. For example, they may be applied to the parts of the plants above or in the soil, or the plant seeds may be contacted with the compound. Alternatively, the compound may be introduced into the soil near the roots of the plants or applied to the surface of the soil and then mixed into the soil to the desired depth.

The amount of the composition that is applied is dependent upon such factors as the species of plant being treated and the plant pathogen whose control is desired and is that amount which will inhibit or prevent the growth of the plant pathogen while causing little or no injury to the plants. About 1 pound to 200 pounds of the active compound is ordinarily applied per acre, with particularly good results being obtained when 5 pounds to 35 pounds per acre is used.

We claim:

1. A method of inhibiting the growth of microorganisms selected from the group consisting of fungi and bacteria, which method comprises applying to said microorganisms an amount to inhibit the growth of said microorganisms of a compound of the formula:

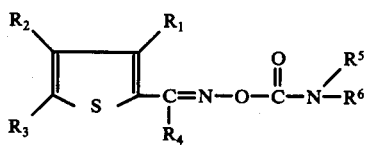

wherein $R_1$ is hydrogen; $R_2$ is hydrogen or $NO_2$; $R_3$ is hydrogen, $NO_2$, halo or $CH_3$; $R_4$ is $CH_3$, $C_2H_5$, $CF_3$, $CH_3S$-cyano or

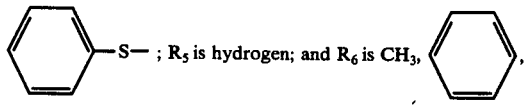

-S—; $R_5$ is hydrogen; and $R_6$ is $CH_3$,

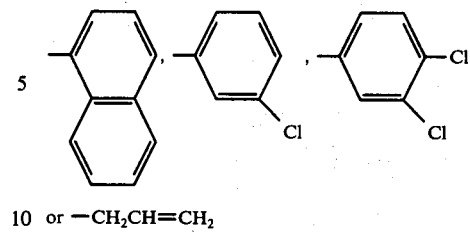

or $-CH_2CH=CH_2$

2. The method of claim 1 where $R_3$ is halo, $R_4$ is $CH_3$, and $R_6$ is

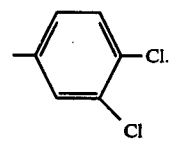

3. The method of claim 1 where $R_3$ is halo, $R_4$ is $CH_3$, and $R_6$ is

4. The method of claim 1 where $R_3$ is halo, $R_4$ is $CH_3S$—, and $R_6$ is $CH_3$.

5. The method of claim 1 where $R_2$ and $R_3$ are hydrogen, $R_4$ is $CH_3$ and $R_6$ is

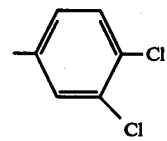

6. The method of claim 1 where $R_3$ is $CH_3$, $R_4$ is $CH_3$ and $R_6$ is ,02/0260

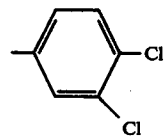

7. The method of claim 1 where $R_2$ and $R_3$ are hydrogen, $R_4$ is cyano and $R_6$ is $CH_3$.

* * * * *